United States Patent
Sheu et al.

(10) Patent No.: US 9,950,028 B2
(45) Date of Patent: Apr. 24, 2018

(54) USES OF STARCH BINDING PROTEIN (SBP)-TAGGED IMMUNOSTIMULATORY PROTEIN

(71) Applicant: Simpson Biotech Co., Ltd, Taoyuan County (TW)

(72) Inventors: Chia-Chin Sheu, Taoyuan County (TW); Chang-Yeu Liu, Taichung (TW)

(73) Assignee: SIMPSON BIOTECH CO., LTD, Taoyuan County (TW)

( * ) Notice: Subject to any disclaimer, the term of this patent is extended or adjusted under 35 U.S.C. 154(b) by 0 days.

(21) Appl. No.: 15/123,425

(22) PCT Filed: Mar. 4, 2015

(86) PCT No.: PCT/CN2015/073622
§ 371 (c)(1),
(2) Date: Sep. 2, 2016

(87) PCT Pub. No.: WO2015/131819
PCT Pub. Date: Sep. 11, 2015

(65) Prior Publication Data
US 2017/0065672 A1    Mar. 9, 2017

Related U.S. Application Data

(60) Provisional application No. 61/947,553, filed on Mar. 4, 2014.

(51) Int. Cl.
| | | |
|---|---|---|
| *A61K 36/074* | (2006.01) |
| *A61K 38/16* | (2006.01) |
| *A61K 36/06* | (2006.01) |
| *A61K 9/00* | (2006.01) |
| *A61K 36/74* | (2006.01) |
| *A61K 47/64* | (2017.01) |

(52) U.S. Cl.
CPC ............ *A61K 38/16* (2013.01); *A61K 9/0053* (2013.01); *A61K 36/06* (2013.01); *A61K 36/074* (2013.01); *A61K 36/74* (2013.01); *A61K 38/168* (2013.01); *A61K 47/646* (2017.08)

(58) Field of Classification Search
CPC ...... A61K 36/06; A61K 36/074; A61K 36/74; A61K 38/16; A61K 38/168; A61K 9/0053; A61K 47/646; A61K 47/4833; C07K 14/00; C07K 2319/00
See application file for complete search history.

*Primary Examiner* — S. Devi
(74) *Attorney, Agent, or Firm* — WPAT, PC

(57) ABSTRACT

The present invention relates to a method for preventing or treating virus and protozoa infection in a subject in need thereof comprising: orally administering to said subject an effective amount of a composition comprising a complex consisting of a starch binding protein (SBP)-tagged immunostimulatory protein and a SBP-binding matrix, wherein the immunostimulatory protein is from *Ganoderma* species. The present invention also relates to a method for inducing interferon-gamma production in a subject in need thereof comprising: orally administering to said subject an effective amount of a composition comprising a complex consisting of a starch binding protein (SBP)-tagged immunostimulatory protein and a SBP-binding matrix, wherein the immunostimulatory protein is from *Ganoderma* species. The present invention further relates to a method for improving feed intake, growth rate or feed conversion ratio in a subject in need thereof comprising: administering to said subject by oral administration or injection an effective amount of a composition comprising a complex consisting of a starch binding protein (SBP)-tagged immunostimulatory protein and a SBP-binding matrix, wherein the immunostimulatory protein is from *Ganoderma* species.

7 Claims, 3 Drawing Sheets

SEQUENCE LISTING

<160> NUMBER OF SEQ ID NOS: 4

<210> SEQ ID NO 1
<211> LENGTH: 318

```
<212> TYPE: DNA
<213> ORGANISM: Rhizopus oryzae
<220> FEATURE:
<221> NAME/KEY: gene
<222> LOCATION: (1)..(318)

<400> SEQUENCE: 1
gcaagtattc ctagcagtgc ttctgtccag cttgattcat acaactacga tggctctact      60
ttttcaggaa aaatttatgt caagaacatt gcttactcca agaaagttac tgtagtctac     120
gccgatggct ctgacaactg gaataataat ggaaacatca ttgctgcttc tttctctggc     180
cctatctctg gatcaaatta cgaatactgg acattctctg cctccgttaa aggtatcaag     240
gagttctaca ttaagtatga agtcagtgga aaaacatact atgataacaa caattctgcc     300
aattaccaag tatctaca                                                   318

<210> SEQ ID NO 2
<211> LENGTH: 333
<212> TYPE: DNA
<213> ORGANISM: Ganoderma lucidum
<220> FEATURE:
<221> NAME/KEY: gene
<222> LOCATION: (1)..(333)

<400> SEQUENCE: 2
atgtccgaca ctgccttgat cttcaggctc gcctgggacg tgaagaagct ctcgttcgac      60
tacaccccga actggggccg cggcaacccc aacaacttca tcgacactgt caccttcccg     120
aaagtcttga ccgacaaggc gtacacgtac cgcgtcgccg tctccggacg gaacctcggc     180
gtgaaaccct cgtacgcggt cgagagcgac ggctcgcaga aggtcaactt cctcgagtac     240
aactccgggt atggcatagc ggacacgaac acgatccagg tgttcgttgt cgaccccgac     300
accaacaacg acttcatcat cgcccagtgg aac                                  333

<210> SEQ ID NO 3
<211> LENGTH: 106
<212> TYPE: PRT
<213> ORGANISM: Rhizopus oryzae
<220> FEATURE:
<221> NAME/KEY: DOMAIN
<222> LOCATION: (1)..(106)

<400> SEQUENCE: 3

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Ile Ile Ala Ala Ser Phe Ser Gly Pro Ile Ser Gly
    50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr
            100                 105

<210> SEQ ID NO 4
<211> LENGTH: 111
<212> TYPE: PRT
```

-continued

```
<213> ORGANISM: Ganoderma lucidum
<220> FEATURE:
<221> NAME/KEY: mat_peptide
<222> LOCATION: (1)..(111)

<400> SEQUENCE: 4

Met Ser Asp Thr Ala Leu Ile Phe Arg Leu Ala Trp Asp Val Lys Lys
1               5                   10                  15

Leu Ser Phe Asp Tyr Thr Pro Asn Trp Gly Arg Gly Asn Pro Asn Asn
                20                  25                  30

Phe Ile Asp Thr Val Thr Phe Pro Lys Val Leu Thr Asp Lys Ala Tyr
            35                  40                  45

Thr Tyr Arg Val Ala Val Ser Gly Arg Asn Leu Gly Val Lys Pro Ser
        50                  55                  60

Tyr Ala Val Glu Ser Asp Gly Ser Gln Lys Val Asn Phe Leu Glu Tyr
65                  70                  75                  80

Asn Ser Gly Tyr Gly Ile Ala Asp Thr Asn Thr Ile Gln Val Phe Val
                85                  90                  95

Val Asp Pro Asp Thr Asn Asn Asp Phe Ile Ile Ala Gln Trp Asn
                100                 105                 110
```

USES OF STARCH BINDING PROTEIN (SBP)-TAGGED IMMUNOSTIMULATORY PROTEIN

FIELD OF THE INVENTION

The present invention relates to effects of administering an immunostimulatory protein from *Ganoderma* species.

BACKGROUND OF THE INVENTION

Starch binding protein (SBP) is a binding domain derived from *Rhizopus oryzae* glucoamylase (RoSBD), a member of carbohydrate-binding module family 21 (CBM21) with raw starch-binding activity. SBP is favorable to be applied as an affinity tag for fusion protein engineering and purification in *Escherichia coli* and *Pichia pastoris* systems. Three amino acid sequences of SBP have been disclosed in U.S. Pat. No. 7,662,918.

*Ganoderma* is a rare and valuable herb in Chinese medicine. It has been known in China for over 5,000 years as "Ling Zhi". There are a variety of *ganodenmas*, including *G. lucidum* (red), *G. applanatum* (brown), *G. tsugae* (red), *G. sinense* (black), and *G. oregonense* (dark brown).

*Ganoderma lucidum* (*Ganoderma lucidum* (Fr.) Karst) is a traditional Chinese medicinal fungi, which has anti-tumor, immuno-modulatory, antiviral, antibacterial, inhibiting platelet aggregation and other effects. It has been found that *Ganoderma lucidum* has anti-allergic activity. (Chen H. Y et al., *J. Med. Mycol.* 1992; 33 505-512) and hepatoprotective effect (Lin J. M. et al., *Am. J. Chin. Med.* 1993; 21(1) 59-69). It has also been found that immune regulatory proteins (LZ-8) purified from *Ganoderma lucidum* has activities of inhibiting systemic allergic reactions, treating liver cancer and preventing diabetes (Kino K. et al., J. Biol. Chem. 1989; 264(1) 472-8). However, LZ-8's application on feed has not been developed yet.

Recently, Yun Cao et al. disclosed that commercially cultivated '*G. lucidum*' ("Lingzhi") in East Asia is a different species from the true *G. lucidum* and proposed a new species *G. lingzhi* for "*Lingzhi*", which has an East Asia distribution (Y. C et. al., Fungal Diversity. 2012; 56(1) 49-62). Therefore, LZ-8 should be deemed as being purified from *Ganoderma lingzhi* rather than *Ganoderma lucidum*. In addition, Fungal immunostimulatory proteins isolated from different *Ganoderma* species have been shown to have similar amino acid sequences and functions. (Lin. W H et. al., J. Biol. Chem. 1997; 272(32):20044-20048., Jinn T R, et. al., Biosci Biotechnol Biochem. 2006; 70(11): 2627-2634.; Huang L et. al., Proteins. 2009; 75(2):524-7).

Interferon (IFN)-gamma is not only a marker of T(H)1 CD4, CD8 and natural killer (NK) cells but also a critical antiviral mediator which is central to the elimination of viruses from the central nervous system (CNS). Interferon-gamma has been associated with various kinds of virus such as measles virus (MV), herpes simplex virus (HSV), vesicular stomatitis virus (VSV) and respiratory syncytial virus. (Chesler D A, Reiss C S. Cytokine Growth Factor Rev. 2002 December; 13(6):441-54; van Schaik S M, Obot N, Enhorning G, Hintz K, Gross K, Hancock G E, Stack A M, Welliver R C. J Med Virol. 2000 October; 62(2):257-66).

Coccidiosis is a parasitic disease of the intestinal tract of animals caused by coccidian protozoa. The disease spreads from one animal to another by contacting with infected feces or ingestion of infected tissue. Diarrhea, which may become bloody in severe cases, is the primary symptom. Most animals infected with coccidia are asymptomatic, but young or immuno-compromised animals may suffer severe symptoms and death. While coccidia can infect a wide variety of animals, including humans, birds, and livestock, they are usually species-specific. In poultry, most coccidiosis was caused by the species belong to the genus *Eimeria* and infect various sites in the intestine. *Coccideosis* is common and widespread in sucking pigs and usually caused by three genus including *Eimeria*, *Isospora* and *Cryptosporidia*.

U.S. Pat. No. 8,163,519 disclosed that fungal immuno-modulatory protein (FIP) protected groupers against Iridovirus or *Vibrio harveyi* infection, but it is administered via intraperitoneal injection of FIP or via feeding FIP-comprising yeast. U.S. Pat. No. 8,163,519 also disclosed that FIP reduced interferon-γ in Der p-stimulated mice, which demonstrated that HP could function in inhibiting anaphylactic. Although U.S. Pat. No. 8,163,519 also disclosed that "splenocytes from Balb/c mice not fed with FIP or from Der p-stimulated mice will produce more IFN-r (463.8 and 1100.7) than the control if re-stimulated with FIP", it is noted that the FIP stimulation was in vitro to the splenocytes directly, which means that this effect may not exist when administering FIP in vivo. Therefore, more experiments are needed to verify the correlation between FIP and interferon-γ in vivo.

Lin et al. (An immunomodulatory protein, Ling Zhi-8, induced activation and maturation of human monocyte-derived dendritic cells by the NF-kappaB and MAPK pathways; J Leukoc Biol. 2009 October; 86(4):877-89.) studied immune modulatory effects of LZ-8 in BALB/c mice by injection and showed that IFN-r was increased. However, this effect may not exist when LZ-8 is administered by oral administration because the complicated chemical reactions in digestive tracts can change LZ-8's structure. Therefore, LZ-8's effect by oral administration can not be easily predicted with results of injection. Further experiments are still needed to verify the correlation between LZ-8 and interferon-γ when orally administering LZ-8 to a subject.

BRIEF DESCRIPTION OF THE DRAWINGS

FIGS. 1A-1C show effect of oral SBP-LZ-8 on Newcastle disease virus (NDV) infection in chicken. FIG. 1A: 1×$LD_{50}$; FIG. 1B: 10×$LD_{50}$; FIG. 1C: 100×$LD_{50}$.

FIG. 2A: 1×$LD_{50}$; FIG. 2B: 10×$LD_{50}$; FIG. 2C: 100×$LD_{50}$.

SUMMARY OF THE INVENTION

Figure 2A:
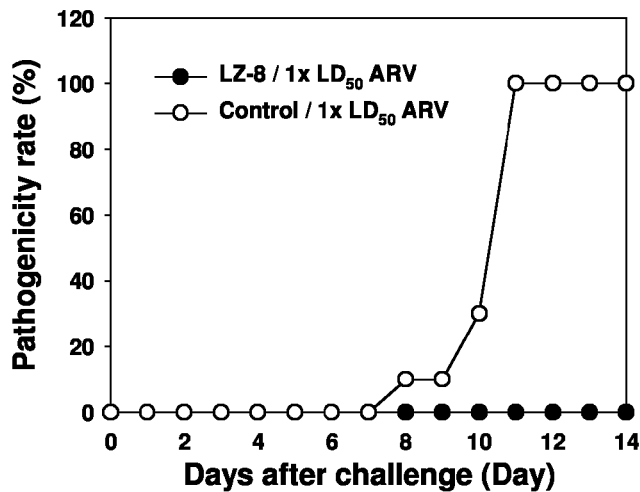
FIGS. 2A-2C show effect of oral SBP-LZ-8 on avian reovirus (ARV) infection in chicken.

The present invention relates to a method for preventing or treating virus and protozoa infection in a subject in need thereof comprising: orally administering to said subject an effective amount of a composition comprising a complex consisting of a starch binding protein (SBP)-tagged immunostimulatory protein and a SBP-binding matrix, wherein the immunostimulatory protein is from *Ganoderma* species. The present invention also relates to a method for inducing interferon-gamma production in a subject in need thereof comprising: orally administering to said subject an effective amount of a composition comprising a complex consisting of a starch binding protein (SBP)-tagged immunostimulatory protein and a SBP-binding matrix, wherein the immunostimulatory protein is from *Ganoderma* species. The present invention further relates to a method for improving feed intake, growth rate or feed conversion ratio in a subject in need thereof comprising: administering to said subject by oral administration or injection an effective amount of a composition comprising a complex consisting of a starch binding protein (SBP)-tagged immunostimulatory protein and a SBP-binding matrix, wherein the immunostimulatory protein is from *Ganoderma* species.

DETAILED DESCRIPTION OF THE INVENTION

The present invention is to investigate the effects of administering a *Ganoderma* species immunostimulatory protein LZ-8 by in vivo experiments, and to examine the possible mechanism of LZ-8 via nutrient utilization and/or immune system. The correlation between LZ-8 administration and virus, bacterial or protozoa infection is also studied.

The terms used in the description herein will have their ordinary and common meaning as understood by those skilled in the art, unless specifically defined otherwise. As used throughout the instant application, the following terms shall have the following meanings:

The term "ug/kg BW/day" refers to "microgram per kilogram body weight per day".

The term "Starch binding protein (SBP)" refers to a binding protein with starch-binding activity.

The term "growth rate" refers to an amount of increase that a specific variable has gained within a specific period and context. In this invention, the specific variable can be weight, volume or size.

The term "feed conversion ratio (FCR)" is a measure of an animal's efficiency in converting feed mass into increases of the desired output. For dairy cows, for example, the output is milk, whereas animals raised for meat—such as beef cows, pigs, chickens, and fish—the output is the mass gained by the animal.

The term "food" refers to all products which can be orally used, such as food, drinks, medicine, nutrient supplements and animal feed.

The term "immunostimulatory protein" refers to a protein which will enhance immune response in a subject.

The present invention provides a method for inducing interferon-gamma production in a subject in need thereof comprising: orally administering to said subject an effective amount of a composition comprising a complex consisting of a starch binding protein (SBP)-tagged immunostimulatory protein and a SBP-binding matrix, wherein the immunostimulatory protein is from *Ganoderma* species. Also, the present invention provides a use of a composition in preparing a pharmaceutical, food, or feed product for inducing interferon-gamma production, wherein the composition comprises a complex consisting of a starch binding protein (SBP)-tagged immunostimulatory protein and a SBP-binding matrix, wherein the immunostimulatory protein is from *Ganoderma* species. Preferably, the *Ganoderma* species is selected from *G. lingzhi, G. lucidum, G. applanatum, G. tsugae, G. sinense* or *G. oregonense*. Preferably, the immunomodulatory protein is LZ-8. In a preferred embodiment, the SBP-tagged immunostimulatory protein is provided by fusing a starch binding protein (SBP) with an immunostimulatory protein. In a preferred embodiment, the SBP-binding matrix is selected from starch, alginate, amylopectin, dextrin resin or amylose resin. In a preferred embodiment, the dosage of the SBP-tagged immunostimulatory protein ranges from 25 ug/kg BW/day to 900 ug/kg BW/day. Preferably, the dosage of SBP-tagged immunostimulatory protein ranges from 50 ug/kg BW/day to 600 ug/kg BW/day. More preferably, the dosage of the SBP-tagged immunostimulatory protein is 100 ug/kg BW/day. In a preferred embodiment, the starch binding protein (SBP) consists of an amino acid sequence of SEQ ID NO: 3; the LZ-8 consists of an amino acid sequence of SEQ ID NO: 4. In a preferred embodiment, the subject is a mammal, bird, fish or shrimp. In an embodiment, the above method enhances the resistance of both virus and protozoa infection in the subject.

The present invention also provides a method for improving feed intake, growth rate or feed conversion ratio in a subject in need thereof comprising: administering to said subject by oral administration or injection an effective amount of a composition comprising a complex consisting of a starch binding protein (SBP)-tagged immunostimulatory protein and a SBP-binding matrix, wherein the immunostimulatory protein is from *Ganoderma* species. Also, the present invention provides a use of a composition in preparing a pharmaceutical, food, or feed product for improving feed intake, growth rate or feed conversion ratio, wherein the composition comprises a complex consisting of a starch binding protein (SBP)-tagged immunostimulatory protein and a SBP-binding matrix, wherein the immunostimulatory protein is from *Ganoderma* species. Preferably, the *Ganoderma* species is selected from *G. lingzhi, G. lucidum, G. applanatum, G. tsugae, G. sinense* or *G. oregonense*. Preferably, the immunomodulatory protein is LZ-8. In a preferred embodiment, the SBP-tagged immunostimulatory protein is provided by fusing a starch binding protein (SBP) with an immunostimulatory protein. In a preferred embodiment, the SBP-binding matrix is selected from starch, alginate, amylopectin, dextrin resin or amylose resin. In a preferred embodiment, the dosage of the SBP-tagged immunostimulatory protein ranges from 25 ug/kg BW/day to 900 ug/kg BW/day. Preferably, the dosage of SBP-tagged immunostimulatory protein ranges from 50 ug/kg BW/day to 600 ug/kg BW/day. More preferably, the dosage of the SBP-tagged immunostimulatory protein is 100 ug/kg BW/day. In a preferred embodiment, the starch binding protein (SBP) consists of an amino acid sequence of SEQ ID NO: 3; the LZ-8 consists of an amino acid sequence of SEQ ID NO: 4. In a preferred embodiment, the subject is a mammal, bird, fish or shrimp.

The present invention further provides a method for preventing or treating virus and protozoa infection in a subject in need thereof comprising: orally administering to said subject an effective amount of a composition comprising a complex consisting of a starch binding protein (SBP)-tagged immunostimulatory protein and a SBP-binding matrix, wherein the immunostimulatory protein is from *Ganoderma* species. Also, the present invention provides a use of a composition in preparing a pharmaceutical, food, or feed product for preventing or treating virus and protozoa infection, wherein the composition comprises a complex consisting of a starch binding protein (SBP)-tagged immunostimulatory protein and a SBP-binding matrix, wherein the immunostimulatory protein is from *Ganoderma* species. Preferably, the *Ganoderma* species is selected from *G. lingzhi, G. lucidum, G. applanatum, G. tsugae, G. sinense* or *G. oregonense*. Preferably, the immunomodulatory protein is LZ-8. In a preferred embodiment, the SBP-tagged immunostimulatory protein is provided by fusing a starch binding protein (SBP) with an immunostimulatory protein. In a preferred embodiment, the SBP-binding matrix is selected from starch, alginate, amylopectin, dextrin resin or amylose resin. In a preferred embodiment, the dosage of the SBP-tagged immunostimulatory protein ranges from 25 ug/kg BW/day to 900 ug/kg BW/day. Preferably, the dosage of SBP-tagged immunostimulatory protein ranges from 50 ug/kg BW/day to 600 ug/kg BW/day. More preferably, the dosage of the SBP-tagged immunostimulatory protein is 100 ug/kg BW/day. In a preferred embodiment, the starch binding protein (SBP) consists of an amino acid sequence of SEQ ID NO: 3; the LZ-8 consists of an amino acid sequence of SEQ ID NO: 4. In a preferred embodiment, the subject is a mammal, bird, fish or shrimp. In a preferred embodiment, the virus infection is by a virus selected from the group consisting of Newcastle disease virus, avian infectious bronchitis virus, Marek's disease virus, avian influenza virus, porcine circovirus, hog cholera virus, swine influenza virus and Lelystad virus. Preferably, the virus infection is by a virus selected from the group consisting of Newcastle disease virus, avian reovirus, and porcine circovirus. In a preferred embodiment, the protozoa infection is coccidiosis. Preferably, the coccidiosis is caused by coccidian protozoa selected from *Eimeria* species. More preferably, the *Eimeria* species is *Eimeria tenella*.

EXAMPLES

The examples below are non-limiting and are merely representative of various aspects and features of the present invention.

Example 1: Preparation of LZ-8 Protein

Construction and Expression of SBP-LZ-8 Protein

The SBP gene (SEQ ID NO: 1) was PCR amplified and fused to the C-terminal of LZ-8. The DNA sequence of LZ-8 was SEQ ID NO: 2. The fused SBP-LZ-8 protein gene was cloned into *Pichia pastoris* expression vector pPICZαA (purchased from Invitrogen) under control of AOX1 promoter and transformed into *Pichia pastoris* X33 (purchased from Invitrogen) for expression. The *Pichia pastoris* transformant harboring SBP-LZ-8 gene was cultivated in BMGY media (100 mM potassium phosphate buffer pH 6.0, 1% glycerol, 1% yeast extract, 2% peptone) for 24 hours. The cells were recovered by centrifugation and resuspended in BMMY media (100 mM potassium phosphate buffer pH 6.0, 0.5% methanol, 1% yeast extract, 2% peptone). Methanol (0.5% v/v) was added every 24 hour in order to induce the expression of SBP-LZ-8. After induction for 3 days, the cells were removed by centrifugation and the cell-free fermentation broth was collected for SDS-PAGE analysis.

Fermentation and Purification of SBP-LZ-8

Transformants expressing SBP-LZ-8 was inoculated in 300 ml YPD (1% yeast extract, 2% peptone and 2% glucose) at 30° C. for 24 hours. The 300 ml of seed culture was inoculated into 100 L fermentor containing 40 L FBS medium [26.7 ml/l $H_3PO_4$ (85% stock), 0.93 g/l $CaSO_4$, 18.2 g/l $K_2SO_4$, 14.9 g/l $MgSO_4 \cdot 7H_2O$, 4.13 g/l KOH and adjusted to pH 5.0 by $NH_4OH$] supplemented with PTM1 trace salts (6 g/l $CuSO_4 \cdot 5H_2O$, 0.08 g/l KI, 3 g/l $MgSO_4 \cdot H_2O$, 0.2 g/l $Na_2MoO_4$, 0.02 g/l $H_3BO_3$, 0.5 g/l $CoCl_2$, 20 g/l $ZnCl_2$, 65 g/l $FeSO_4 \cdot 7H_2O$, 0.2 g/l biotin and 5 ml $H_2SO_4$) and 3% glycerol for batch fermentation about 24 h after the glycerol was exhausted which was indicated by the rapid increase of dissolved oxygen (DO). The glycerol feeding was then proceeded for 24 h and the $OD_{600}$ increased over 500 at the end of fed-batch process. The expression of SBP-LZ-8 was induced by methanol feeding after glycerol fed-batch and lasted for 4 days. Appropriate amount of starch was added into the cell free fermentation supernatant for the purification of SBP-LZ-8 due to the specific interaction between starch and SBP tag. The SBP-LZ-8 bound starch was recovered and dried. The SBP-LZ-8 could be eluted from starch by 10 mM glycine-HCl buffer pH 11.0 for protein concentration quantification using BCA method (Pierce). SBP-LZ-8 was a fusion protein of SBP (SEQ ID NO: 3) and LZ-8 (SEQ ID NO: 4) which maintained LZ-8 activities and was used in following examples.

Example 2: Effect of LZ-8 on Growth Performance in Post-Weaning Pig

Material and Methods

This trial was conducted at the experimental farm of the Animal Technology Institute Taiwan. The farm was a commercial swine farm with some pens designed and used for research. Therefore, the management and the environment were consistent for all pigs for research and production.

Animal and Treatment

Total 36 crossbred pigs (body weight 7.8 kg) were randomly divided into 3 groups with 3 pens and 4 pigs/pen for each group: (1) control without the SBP-LZ-8 additive, (2) low dosage of SBP-LZ-8 (100 ug/kg BW/day), and (3) high dosage of SBP-LZ-8 (600 ug/kg BW/day). Pigs were fed a mesh diet (antibiotics added) for 28 days. The feed formulation and nutrient contents were listed in Table 1.

TABLE 1

The composition and nutrient contents of experimental diet

| Ingredient | kg/ton |
| --- | --- |
| Corn | 619.3 |
| SBM (43% CP) | 240 |
| Fish meal (65% CP) | 25 |
| Milk replacer (38% CP) | 25 |
| Fermented plant protein (60% CP) | 25 |
| Soybean oil | 30 |
| Limestone | 10 |
| Monocalcium phosphate | 12 |
| Salt | 4 |
| Lysine | 1.5 |
| Methionine | 1.5 |
| Threonine | 1 |
| Choline chloride | 1 |
| Vitamin premix | 1 |
| Mineral premix | 1 |
| Acidifier | 1 |
| Antibiotics[1] | 1.7 |
| Chemical composition | |
| ME (Kcal/kg) | 3,320 |
| Crude protein (%) | 19.3 |
| Lys (%) | 1.19 |
| Ca (%) | 0.79 |
| Total P (%) | 0.64 |

[1]STP-500 (1.2 kg) and Carbadox (0.5 kg) were added to a ton of feed.

Measurements

Individual pigs were weighed at the beginning and at the end of the trial. Body weight and feed consumption were recorded for each pen to calculate average daily gain (ADG), average daily feed intake (ADFI) and feed conversion ratio (FCR, ADFI/ADG).

On day 14 and 28, blood samples were collected from one barrow and one gilt per pen to determine glucose, BUN, triglycerides (Kodak Ektachem DT-II System, Rochester, N.Y.) and interferon-γ (ELISA kit, Invitrogen, CA) levels.

Statistics

The data were analyzed with the GLM procedure of SAS (SAS Inst. Inc., Cary, N.C., USA). The pen was used as the experimental unit for analysis of growth parameters, and the pig was used as the experimental unit for analysis of blood parameters.

Results

Survival Rate

In this trial, antibiotics (STP-500 and Carbadox) were added to the diets. During the trial, no pigs died or were culled. So, this trial was not able to determine the effect of SBP-LZ-8 on survival rate among groups (Table 2).

TABLE 2

Effect of SBP-LZ-8 on growth performance and survival rate of post-weaning pigs

| Item | Control | SBP-LZ-8 (100 ug/kg BW) | SBP-LZ-8 (600 ug/kg BW) |
|---|---|---|---|
| Initial BW, kg | 7.7 | 7.8 | 7.8 |
| Final BW, kg | 19.6 | 21.2* | 20.2 |
| ADG, g/day | 425 | 481* (+13.2%) | 445 (+4.7%) |
| ADFI, g/day | 656 | 720 (+9.8%) | 681 (+3.8%) |
| FCR, ADFI/ADG | 1.543 | 1.497 (−3.0%) | 1.531 (−0.8%) |
| Survival rate, % (Culled/total) | 100 (0/12) | 100 (0/12) | 100 (0/12) |

N = 3 (Three pens for each group with 4 pigs/pen in a 4-week trial).
(*P < 0.05)

Growth Performance

According to the daily feed intake of the pigs, the amount of SBP-LZ-8 added to the diet was designed to be constant to keep the intake of SBP-LZ-8 at 100 ug or 600 ug/kg BW.

The supplement of SBP-LZ-8 stimulated ADG, which was significant (P<0.05) at 100 ug/kg BW (+13.2%, Table 2). Although no statistical significance was detected (P>0.05), SBP-LZ-8 at 100 ug/kg BW also increased ADFI by 9.8% and improved FCR by 3.0%. The effects of SBP-LZ-8 at 600 ug/kg BW on feed intake was less than SBP-LZ-8 at 100 ug/kg BW. However, some improvements in ADG (+4.7%) and ADFI (+3.8%) were observed. Higher dosage of SBP-LZ-8 (600 g/kg BW) might over-stimulate the immune system resulting in energy and protein deprivation. Therefore, its effect on the growth performance was less significant than low SBP-LZ-8 dosage at 100 ug/kg BW. In this trial, it was found that with antibiotics added in the diet SBP-LZ-8 (100 ug/kg BW) improved growth performance in post-weaning pigs, including feed intake, growth rate, and feed utilization.

At the end of the trial, pigs fed with SBP-LZ-8 at 100 ug/kg BW had 1.6 kg higher body weight than the control group (P<0.05). High SBP-LZ-8 dosage (600 ug/kg BW) only increased weight gain by 0.6 kg.

Blood Parameters

There were no differences in levels of glucose, BUN or triglycerides among groups on d 14 and 28 (Table 3). Pigs fed with SBP-LZ-8 at 100 ug/kg BW tended to have higher glucose levels than the control group (P<0.1).

TABLE 3

Effect of SBP-LZ-8 on blood parameters of post-weaning pigs

| Item | Control | SBP-LZ-8 (100 ug/kg BW) | SBP-LZ-8 (600 ug/kg BW) |
|---|---|---|---|
| Glucose (mg/dL) | | | |
| d 14 | 88 | 104 | 91 |
| d 28 | 104 | 109 | 107 |
| BUN (mg/dL) | | | |
| d 14 | 9.5 | 9.8 | 11.2 |
| d 28 | 11.2 | 10.3 | 10.7 |
| Triglycerides (mg/dL) | | | |
| d 14 | 37.3 | 28.3 | 25.8 |
| d 28 | 24.5 | 27.3 | 37.0 |
| Interferon-γ (pg/ml) | | | |
| d 14 | 12.0 | 24.4* | 26.5** |
| d 28 | 11.7 | 19.0 | 29.3** |

(*P < 0.05, **P < 0.01)

For interferon-γ, dietary SBP-LZ-8 stimulated interferon-γ production (Table 3). After feeding SBP-LZ-8 for 14 days, SBP-LZ-8 at 100 ug/kg BW increased interferon-γ levels by 103% (P<0.05), and SBP-LZ-8 at 600 ug/kg BW had similar effect on interferon-γ with 120% higher than the control group (P<0.01). On d 28, SBP-LZ-8 (100 ug/kg BW) increased interferon-γ levels by 62% (P>0.05), and high SBP-LZ-8 dosage (600 ug/kg BW) maintained the same effect on interferon-γ with 150% higher than the control group (P<0.01). So, high SBP-LZ-8 dosage could prolong the effect on interferon-γ.

In this study, dietary supplement with SBP-LZ-8 was beneficial for weanling pig growth. The effect of SBP-LZ-8 on growth was not related to digestion and absorption since no changes in blood glucose, BUN or triglycerides were found. As for improving growth performance in post-weaning pigs, the dosage of SBP-LZ-8 at 100 ug/kg BW had a better effect than high dosage at 600 ug/kg BW.

Example 3: Effect of LZ-8 on Growth Performance in Post-Weaning Pig (Without Antibiotics)

Material and Methods

This trial was conducted at the experimental farm of the Animal Technology Institute Taiwan. The farm was a commercial swine farm with some pens designed and used for research. Therefore, the management and the environment were consistent for all pigs for research and production.

Animal and Treatment

Total 80 weaned pigs (body weight 8.0 kg) were randomly divided into 4 groups with 5 pens and 4 pigs/pen for each group: (1) positive control with antibiotics (STP-500 and Carbadox), (2) negative control without antibiotics, (3) low dosage of SBP-LZ-8 (50 ug/kg BW/day) without antibiotics, and (4) high dosage of SBP-LZ-8 (100 ug/kg BW/day) without antibiotics. Pigs were fed with a mesh diet for 28 days. The feed formulation and nutrient contents were listed in Table 4.

TABLE 4

The composition and nutrient contents of experimental diet

| Ingredient | kg/ton |
| --- | --- |
| Corn | 600 |
| SBM (43% CP) | 210 |
| Fish meal (65% CP) | 50 |
| Milk replacer (38% CP) | 50 |
| Fermented plant protein (60% CP) | 25 |
| Soybean oil | 30 |
| Limestone | 10 |
| Monocalcium phosphate | 12 |
| Salt | 4 |
| Lysine | 1.5 |
| Methionine | 1.2 |
| Threonine | 0.6 |
| Choline chloride | 1 |
| Vitamin premix | 1 |
| Mineral premix | 1 |
| Acidifier | 1 |
| Antibiotics[(1)] | +/−1.7 |
| Chemical composition | |
| ME (Kcal/kg) | 3,310 |
| Crude protein (%) | 20.1 |
| Lys (%) | 1.30 |
| Ca (%) | 0.88 |
| Total P (%) | 0.69 |

[(1)]STP-500 (1.2 kg) and Carbadox (0.5 kg) were added to a ton of feed only for positive control group.

Measurements

Individual pigs were weighed at the beginning and at the end of the trial. Body weight and feed consumption were recorded for each pen to calculate average daily gain (ADG), average daily feed intake (ADFI) and feed conversion ratio (FCR, ADFI/ADG).

On day 14 and 28, blood samples were collected from one barrow and one gilt per pen to determine glucose, BUN, triglycerides (Kodak Ektachem DT-II System, Rochester, N.Y.) and interferon-γ (ELISA kit, Invitrogen, CA) levels.

Statistics

The data were analyzed by using the GLM procedure of SAS (SAS Inst. Inc., Cary, N.C., USA). The pen was used as the experimental unit for analysis of growth parameters, and the pig was used as the experimental unit for analysis of blood parameters.

Results

Survival Rate

The survival rate was around 90-95% among groups. Diets with or without antibiotics or SBP-LZ-8 had no effect on survival rate of post-weaning pigs (Table 5).

TABLE 5

Effect of SBP-LZ-8 on growth performance and survival rate of post-weaning pigs

| Item | Positive (with antibiotics) | Negative (without antibiotics) | SBP-LZ-8 50 ug/kg BW (without antibiotics) | SBP-LZ-8 100 ug/kg BW (without antibiotics) |
| --- | --- | --- | --- | --- |
| Initial BW, kg | 8.0 | 8.1 | 8.1 | 8.0 |
| Final BW, kg | 19.3[a] | 16.9[c] | 16.9[c] | 18.0[b] |
| ADG, g/day | 324[a] | 251[c] (−22.5%) | 254[c] (−21.6%) | 285[b] (−12.0%) |
| ADFI, g/day | 507[a] | 410[b] (−19.1%) | 403[b] (−20.5%) | 429[b] (−15.4%) |
| FCR, | 1.565[b] | 1.634[c] | 1.587[bc] | 1.506[a] |
| ADFI/ADG | | (+4.4%) | (+1.4%) | (−3.8%) |
| Survival rate, % (Culled/total) | 95% (1/20) | 90% (2/20) | 95% (1/20) | 95% (1/20) |

N = 5 (Five pens for each group with 4 pigs/pen in a 5-week trial).
Antibiotics were STP500 and Carbadox (a vs. b, $P < 0.05$; a vs. c, $P < 0.001$; b vs. c, $P < 0.05$)

Growth Performance

Compared with the positive control, pigs fed a diet without antibiotics had lower ADG (−22.5%, $P<0.001$), ADFI (−19.1%, $P<0.05$) and higher FCR (+4.4%, $P<0.05$).

Without antibiotics, SBP-LZ-8 supplement at 50 ug/kg BW had no effect on growth performance SBP-LZ-8 at 100 ug/kg BW stimulated ADG by 13.5% ($P<0.05$) and improved FE by 8.5% ($P<0.001$) as compared with the negative control. Although the performance of ADG and ADFI was not as good as the positive control, the FCR of SBP-LZ-8 group performed better (−3.8%, $P<0.05$). Therefore, it was possible to improve growth performance, including ADG and FCR, in weanling pigs without antibiotic addition.

Blood Parameters

There were no differences in levels of glucose, BUN or triglycerides among groups on d 14 and 28 (Table 6).

TABLE 6

Effect of SBP-LZ-8 on blood parameters of post-weaning pigs

| Item | Positive (with antibiotics) | Negative (without antibiotics) | SBP-LZ-8 50 ug/kg BW (without antibiotics) | SBP-LZ-8 100 ug/kg BW (without antibiotics) |
| --- | --- | --- | --- | --- |
| Glucose (mg/dL) | | | | |
| d 14 | 102 | 97 | 102 | 99 |
| d 28 | 106 | 102 | 101 | 102 |
| BUN (mg/dL) | | | | |
| d 14 | 12.3 | 12.6 | 11.3 | 11.8 |
| d 28 | 11.7 | 10.9 | 12.0 | 12.5 |
| Triglycerides (mg/dL) | | | | |
| d 14 | 30.2 | 28.9 | 21.5 | 21.0 |
| d 28 | 26.3 | 24.5 | 25.3 | 24.0 |
| Interferon-γ (pg/ml) | | | | |
| d 14 | 16.2 | 15.8 | 15.4 | 22.7** |
| d 28 | 17.1 | 16.6 | 19.2 | 22.5* |

(*$P < 0.05$, $P < 0.01$, *$P < 0.001$)

As for interferon-γ, groups without antibiotics (negative control, 50 ug) had similar interferon-γ levels to that of the positive control ($P>0.05$). However, SBP-LZ-8 at 100 ug/kg BW had some effects on interferon-γ production (Table 6). After being fed with SBP-LZ-8 at 100 ug/kg BW for 14 days, interferon-γ levels were increased by 40% ($P<0.01$).

And on d 28, SBP-LZ-8 at 100 ug/kg BW increased interferon-γ levels by 32% (P<0.05). So, in the antibiotics-free diet, long term feeding of SBP-LZ-8 would stimulate interferon-γ production or secretion.

In this study, pigs fed with antibiotics-free diets had low performance. The supplementation with SBP-LZ-8 to antibiotics-free diets improved growth performance. The effect of SBP-LZ-8 might not be related to nutrition and digestion, since blood glucose, BUN or triglycerides were not affected. In this study, it was found that, without antibiotics, the dosage of SBP-LZ-8 at 100 ug/kg BW had a beneficial effect on growth performance in post-weaning pigs.

Example 4: Effect of LZ-8 on Growth Performance and Porcine Circovirus Type 2 (PCV2) Antibody Titer in Post-Weaning Pigs Porcine circovirus type 2 or PCV2 is a very small DNA virus that infected pigs specifically. This experiment was to investigate the effects of SBP-LZ-8 supplemented diet on growth performance and survival rate of post-weaning pigs infected with PCV2 on a commercial environment to examine if the supplement of SBP-LZ-8 was beneficial to swine production.

Material and Methods

This trial was conducted at a commercial farm in Yunlin county (Taiwan) with 2,000 hogs marketed per year. It was known that almost all swine farms in Taiwan were infected by PCV2. Purchased pigs were tested for their PCV2 antibody titer during the adaption period. Pigs with PCV2 antibody (considered to be infected) were selected for this experiment. After a week of adaption, 200 post-weaning pigs purchased from a commercial breeding farm nearby were selected for experiment.

Animal and Treatment

Pigs (average body weight 10.4 kg) were randomly divided into control and SBP-LZ-8 group (100 ug/kg BW/day) with 5 pens (20 pigs/pen) for each group. Pigs were fed with a commercial mesh post-weaning diet (antibiotics added) for 28 days and a mesh grower diet for another 28 days. The trial lasted 56 days. The nutrient contents of the diets were listed in Table 7.

TABLE 7

The nutrient contents of experimental diets

| Item | Post-weaning diet | Grower diet |
|---|---|---|
| Crude protein (%) | 21.2 | 19.5 |
| Lysine (%) | 1.45 | 1.22 |
| Ca (%) | 0.83 | 0.89 |
| Total P (%) | 0.67 | 0.64 |

Measurements

Pigs from one pen were weighed in a group at the beginning and at the end of each phase. Body weight and feed consumption were recorded for each pen to calculate average daily gain (ADG), average daily feed intake (ADFI) and feed conversion ratio (FCR, ADFI/ADG).

On day 28 and 56, blood samples were collected from 10 pigs of each pen to determine the interferon-γ levels.

Statistics

The data were analyzed with the GLM procedure of SAS (SAS Inst. Inc., Cary, N.C., USA). The pen was used as the experimental unit for analysis of growth parameters, and the pig was used as the experimental unit for analysis of blood parameters.

Results

Growth Performance and Survival Rate

The supplement of SBP-LZ-8 stimulated AGFI by 5.4% and increased ADG by 7.3% during the first phase (d 1-28). However, the differences were not significant (P>0.05) between the control and the treatment (Table 8). The number of pigs died or culled from the trial was higher in the control group (14) than that of the treatment (6). So, SBP-LZ-8 supplement improved survival rate of post-weaning pigs by 8%.

TABLE 8

Effect of SBP-LZ-8 on growth performance and survival rate of post-weaning pigs on commercial farm

| Item | Control | SBP-LZ-8 |
|---|---|---|
| Initial BW, kg | 10.53 | 10.22 |
| d 28 BW, kg | 21.64 | 22.14 |
| d 56 BW, kg | 34.71 | 36.48* |
| d 1-28 | | |
| ADFI, g/day | 625 | 659 |
| ADG, g/day | 397 | 426 |
| FCR, ADFI/ADG | 1.574 | 1.542 |
| Survival rate, % | 86 | 94 |
| d 29-56 | | |
| ADFI, g/day | 972 | 1,042 |
| ADG, g/day | 467 | 512* |
| FCR, ADFI/ADG | 2.082 | 2.035 |
| Survival rate, % | 82 | 92 |

N = 5 (Five pens for each group with 20 pigs/pen in a 8-week trial).
(*P < 0.05)

During the second phase (d 29-56), SBP-LZ-8 supplement consistently stimulated ADFI by 7.2% (P>0.05) and improved ADG by 9.6% (P<0.05). SBP-LZ-8 supplement slightly decreased the FCR although the difference was not significant between control and treatment. Compared to the first phase, the number of pigs died or culled from the trial was less in the second phase. The treatment remained a better survival rate than the control group (Table 8).

Therefore, the supplement of SBP-LZ-8 in post-weaning and grower diets for 56 days stimulated feed intake and improved final weigh by 1.77 kg (P<0.05). The higher survival rate of the SBP-LZ-8 supplement indicated that SBP-LZ-8 is effective in treating PCV2, and also indicated more pigs for marketing and cost saving.

Blood Parameters

The levels of interferon-γ were significantly (P<0.05) higher in SBP-LZ-8 group after feeding for 56 days (Table 9).

TABLE 9

Effect of SBP-LZ-8 on blood parameters of post-weaning pigs on commercial farm

| Interferon-γ (pg/ml) | Control | SBP-LZ-8 |
|---|---|---|
| d 28 | 24.47 | 31.05 |
| d 56 | 18.35 | 25.71* |

(*P < 0.05)

Figures 1A, 1B, 1C:
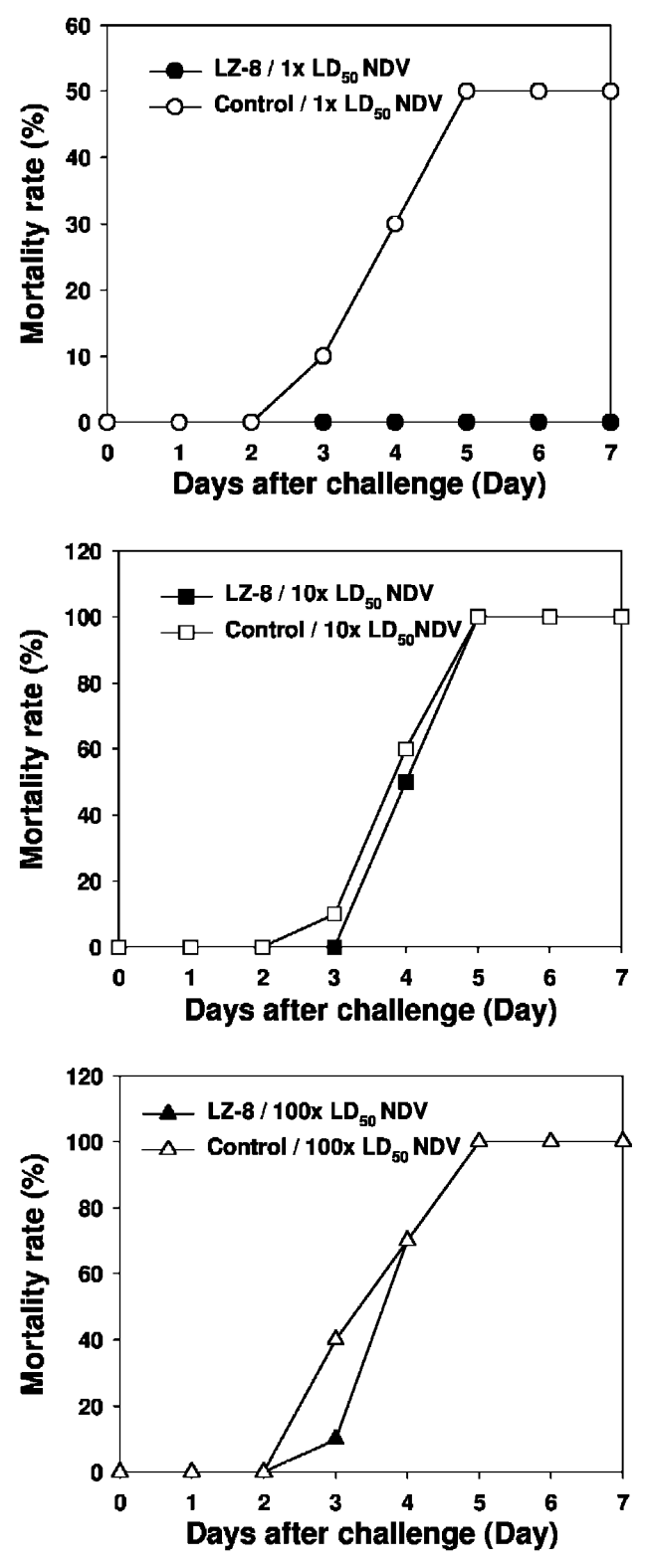
Figure 2B:
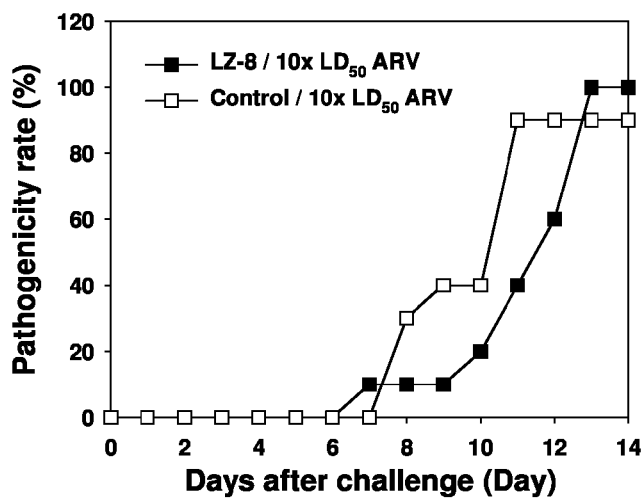
Figure 2C:
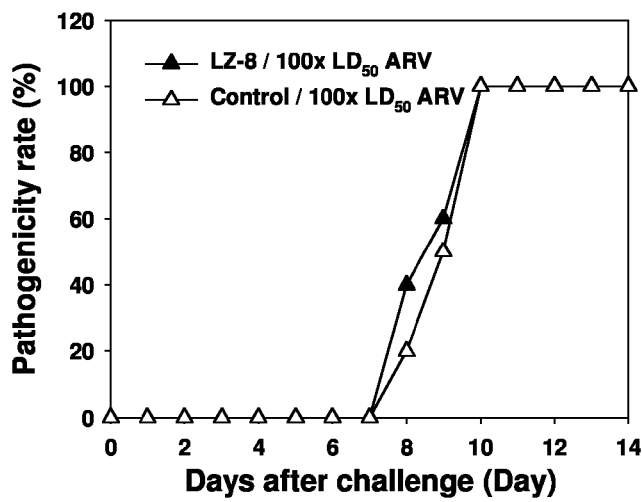

Example 5: Effect of Oral SBP-LZ-8 on Newcastle Disease Virus (NDV) Infection in Chicken SBP-LZ-8 was added to commercial feed without antibiotics to a concentration of 100 μg/kg BW and fed to chickens for a week before challenging with $1\times LD_{50}$, $10\times LD_{50}$ or $100\times LD_{50}$ NDV Sato by injection. Results were shown in Table 10 and FIGS. 1A-1C. Under high dose challenge ($10\text{-}100\times LD_{50}$) of NDV, although 100% mortality was observed on day 7 for both groups with and without SBP-LZ-8, SBP-LZ-8 supplementation did delay the onset of disease. No death was observed in chickens fed with SBP-LZ-8 after $1\times LD_{50}$ NDV challenge. In the group without SBP-LZ-8, 10% mortality rate was observed on day 3 after $1\times LD_{50}$ NDV challenge, 30% on day 4, and 50% on day 7. The result indicated that oral administration of SBP-LZ-8 prevented any death while the control group resulted in 50% death in day 7 under low dose challenge ($1\times LD_{50}$ NDV). These experiments were done when the chickens showed no NDV antibodies (HI<2). Thus, SBP-LZ-8 exhibited anti-NDV activities, including delayed disease onset and reduced mortality rate.

for a week before challenging with $10^3$ ($1\times LD_{50}$), $10^4$ ($10\times LD_{50}$) or $10^5$ ($100\times LD_{50}$) TCID50 ARV 1733 by foot pad injection. Results were shown in Table 11 and FIGS. 2A-2C. When $10^5$ ARV was used for challenge, in both groups with and without SBP-LZ-8, signs of disease such as swollen joints and limping were observed starting on day 8 and 100% of the chickens showed signs by day 11. When $10^4$ ARV was used for challenge, in both groups with and without SBP-LZ-8, signs of disease such as swollen joints and limping were observed starting on day 7-8. On day 13, 100% of the chickens showed signs in the SBP-LZ-8 group while 90% showed signs in the control group. When $10^3$ ARV was used for challenge, in the group with SBP-LZ-8, no signs of disease such as swollen joints and limping were observed on day 14. For the control group, 10% of the chickens showed clinical signs on day 8 and 100% showed signs by day 11. These results indicated that SBP-LZ-8 provides complete protection against low dose ARV challenge, but protection was not obvious for high dose challenges.

TABLE 10

| Treatment | challenge does | | 1 | 2 | 3 | 4 | 5 | 6 | 7 |
|---|---|---|---|---|---|---|---|---|---|
| | | | Days after challenging/cumulated death (n = 20) | | | | | | |
| SBP-LZ-8 | 100x $LD_{50}$ | LZ-8/100x $LD_{50}$ NDV | 0 | 0 | 2 | 14 | 20 | 20 | 20 |
| — | 100x $LD_{50}$ | Control/100x $LD_{50}$ NDV | 0 | 0 | 8 | 14 | 20 | 20 | 20 |
| SBP-LZ-8 | 10x $LD_{50}$ | LZ-8/10x $LD_{50}$ NDV | 0 | 0 | 0 | 10 | 20 | 20 | 20 |
| — | 10x $LD_{50}$ | Control/10x $LD_{50}$ NDV | 0 | 0 | 2 | 12 | 20 | 20 | 20 |
| SBP-LZ-8 | 1x $LD_{50}$ | LZ-8/1x $LD_{50}$ NDV | 0 | 0 | 0 | 0 | 0 | 0 | 0 |
| — | 1x $LD_{50}$ | Control/1x $LD_{50}$ NDV | 0 | 0 | 2 | 6 | 10 | 10 | 10 |
| | | | Days after challenging/cumulated mortality (%) | | | | | | |
| SBP-LZ-8 | 100x $LD_{50}$ | LZ-8/100x $LD_{50}$ NDV | 0 | 0 | 10 | 70 | 100 | 100 | 100 |
| — | 100x $LD_{50}$ | Control/100x $LD_{50}$ NDV | 0 | 0 | 40 | 70 | 100 | 100 | 100 |
| SBP-LZ-8 | 10x $LD_{50}$ | LZ-8/10x $LD_{50}$ NDV | 0 | 0 | 0 | 50 | 100 | 100 | 100 |
| — | 10x $LD_{50}$ | Control/10x $LD_{50}$ NDV | 0 | 0 | 10 | 60 | 100 | 100 | 100 |
| SBP-LZ-8 | 1x $LD_{50}$ | LZ-8/1x $LD_{50}$ NDV | 0 | 0 | 0 | 0 | 0 | 0 | 0 |
| — | 1x $LD_{50}$ | Control/1x $LD_{50}$ NDV | 0 | 0 | 10 | 30 | 50 | 50 | 50 |

Example 6: Effect of Oral SBP-LZ-8 on Avian Reovirus (ARV) Infection in Chicken

SBP-LZ-8 was added to commercial feed without antibiotics to a concentration of 100 μg/kg BW and fed to chickens

TABLE 11

| Treatment | challenge does | | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | | Days after challenging/cumulative diseased chickens (n = 10) | | | | | | | | | | | | | |
| SBP-LZ-8 | 100x $LD_{50}$ | LZ-8/100x $LD_{50}$ ARV | 0 | 0 | 0 | 0 | 0 | 0 | 0 | 4 | 6 | 10 | 10 | 10 | 10 | 10 |
| — | 100x $LD_{50}$ | Control/100x $LD_{50}$ ARV | 0 | 0 | 0 | 0 | 0 | 0 | 0 | 2 | 5 | 10 | 10 | 10 | 10 | 10 |
| SBP-LZ-8 | 10x $LD_{50}$ | LZ-8/10x $LD_{50}$ ARV | 0 | 0 | 0 | 0 | 0 | 0 | 1 | 1 | 1 | 2 | 4 | 6 | 10 | 10 |
| — | 10x $LD_{50}$ | Control/10x $LD_{50}$ ARV | 0 | 0 | 0 | 0 | 0 | 0 | 0 | 3 | 4 | 4 | 9 | 9 | 9 | 9 |
| SBP-LZ-8 | 1x $LD_{50}$ | LZ-8/1x $LD_{50}$ ARV | 0 | 0 | 0 | 0 | 0 | 0 | 0 | 0 | 0 | 0 | 0 | 0 | 0 | 0 |
| — | 1x $LD_{50}$ | Control/1x $LD_{50}$ ARV | 0 | 0 | 0 | 0 | 0 | 0 | 0 | 1 | 1 | 3 | 10 | 10 | 10 | 10 |
| | | | Days after challenging/cumulated pathogenicity (%) | | | | | | | | | | | | | |
| SBP-LZ-8 | 100x $LD_{50}$ | LZ-8/100x $LD_{50}$ ARV | 0 | 0 | 0 | 0 | 0 | 0 | 0 | 40 | 60 | 100 | 100 | 100 | 100 | 100 |
| — | 100x $LD_{50}$ | Control/100x $LD_{50}$ ARV | 0 | 0 | 0 | 0 | 0 | 0 | 0 | 20 | 50 | 100 | 100 | 100 | 100 | 100 |
| SBP-LZ-8 | 10x $LD_{50}$ | LZ-8/10x $LD_{50}$ ARV | 0 | 0 | 0 | 0 | 0 | 0 | 10 | 10 | 10 | 20 | 40 | 60 | 100 | 100 |
| — | 10x $LD_{50}$ | Control/10x $LD_{50}$ ARV | 0 | 0 | 0 | 0 | 0 | 0 | 30 | 40 | 40 | 90 | 90 | 90 | 90 | 90 |
| SBP-LZ-8 | 1x $LD_{50}$ | LZ-8/1x $LD_{50}$ ARV | 0 | 0 | 0 | 0 | 0 | 0 | 0 | 0 | 0 | 0 | 0 | 0 | 0 | 0 |
| — | 1x $LD_{50}$ | Control/1x $LD_{50}$ ARV | 0 | 0 | 0 | 0 | 0 | 0 | 10 | 10 | 30 | 100 | 100 | 100 | 100 | 100 |

Example 7: Effect of Oral SBP-LZ-8 on Avian Coccidia Infection in Chicken

Figure 3:
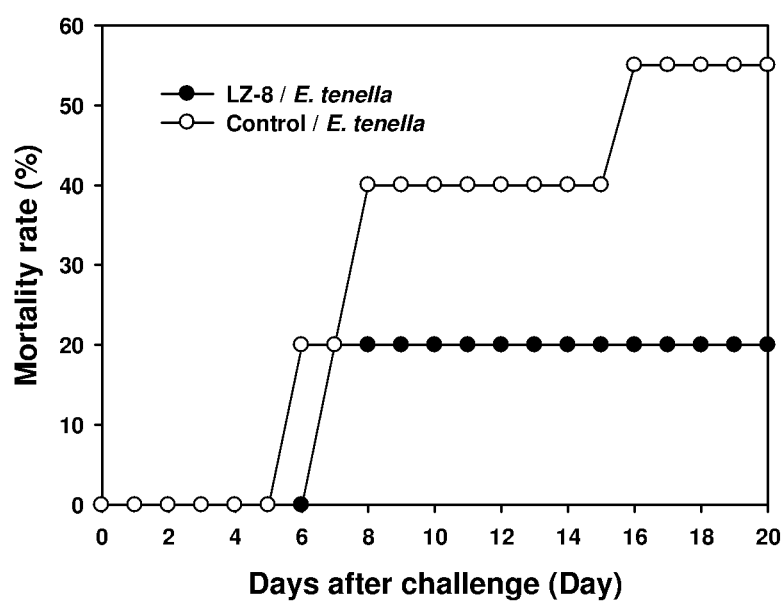
FIG. 3 shows effect of oral SBP-LZ-8 on avian coccidia infection in chicken.

SBP-LZ-8 was added to commercial feed without antibiotics to a concentration of 100 µg/kg BW and fed to chickens for a week before challenging with 10,000 *Eimeria tenella* oocyst by oral. Results were shown in Table 12 and FIG. 3. In the group with SBP-LZ-8, 20% mortality rate was observed on day 7 until day 20 after challenge. In the group without SBP-LZ-8, 20% mortality rate was observed on day 6 after challenge, 40% on day 8, and 55% on day 20. The result indicated that oral administration of SBP-LZ-8 significantly delayed the disease onset ant reduced mortality rate.

TABLE 12

| Treatment | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| | Days after challenging/cumulated death (n = 20) | | | | | | | | | | | | | | | | | | | |
| SBP-LZ-8 | 0 | 0 | 0 | 0 | 0 | 0 | 4 | 4 | 4 | 4 | 4 | 4 | 4 | 4 | 4 | 4 | 4 | 4 | 4 | 4 |
| — | 0 | 0 | 0 | 0 | 0 | 4 | 4 | 8 | 8 | 8 | 8 | 8 | 8 | 8 | 8 | 11 | 11 | 11 | 11 | 11 |
| | Days after challenging/cumulated mortality (%) | | | | | | | | | | | | | | | | | | | |
| SBP-LZ-8 | 0 | 0 | 0 | 0 | 0 | 0 | 20 | 20 | 20 | 20 | 20 | 20 | 20 | 20 | 20 | 20 | 20 | 20 | 20 | 20 |
| — | 0 | 0 | 0 | 0 | 0 | 20 | 20 | 40 | 40 | 40 | 40 | 40 | 40 | 40 | 40 | 55 | 55 | 55 | 55 | 55 |

Example 8: Anti-Viral Activity of Orally Administration of LZ-8

In a non official field test, 20,000 laying hens grew in avian influenza virus epidemic area was treated with SBP-LZ-8. The production of eggs was significantly decreased up to 30% reduction during avian influenza epidemic season without SBP-LZ-8 supplementation. The laying hens were fed with feed containing SBP-LZ-8 at a concentration of 100 □g/kg BW and the egg production rate was recovered to normal level after 3-7 days of SBP-LZ-8 treatment.

In another experiment, 2000 laying hens infected by Marek's Disease were fed with feed containing SBP-LZ-8 at a concentration of 100 □g/kg BW while another 2000 Marek's Disease laying hens were fed with feed without SBP-LZ-8 supplementation. Over 300 hens died in growing period without SBP-LZ-8 supplementation and less than 20 hens died in the group fed with SBP-LZ-8.

SBP-LZ-8 was also tested in a 2000 growing-finishing pig farm. The mortality rate of post-weaning pigs bought was 15% due to immune problem, and the survived had slow weight gain. After being fed with SBP-LZ-8 at the concentration of 100 ug/kg BW for one month, the mortality rate was reduced to 6% and better growth performance was observed in the survived healthy pigs.

These data suggested that orally administration of SBP-LZ-8 might facilitate the virus resistant of animals due to the stimulation the IFN-γ production.

One skilled in the art readily appreciates that the present invention is well adapted to carry out the objects and obtain the ends and advantages mentioned, as well as those inherent therein. The compositions, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of enhancing resistance against protozoa infection in an animal in need thereof comprising orally administering to said animal an effective amount of a composition comprising a complex consisting of a starch binding protein (SBP) that is fused to an immunostimulatory protein and a SBP-binding matrix, wherein the protozoa infection is coccidiosis caused by *Eimeria* species, wherein the SBP consists of the amino acid sequence of SEQ ID NO: 3 and the immunomodulatory protein consists of the amino acid sequence of SEQ ID NO: 4.

2. The method of claim 1, wherein the dosage of the SBP that is fused to the immunostimulatory protein ranges from 25 microgram per kilogram body weight per day to 900 microgram per kilogram body weight per day.

3. A method of inducing interferon-gamma production in an animal in need thereof comprising orally administering to said animal an effective amount of a composition comprising a complex consisting of a starch binding protein (SBP) that is fused to an immunostimulatory protein and a SBP-binding matrix, wherein the SBP consists of the amino acid sequence of SEQ ID NO: 3 and the immunomodulatory protein consists of the amino acid sequence of SEQ ID NO: 4.

4. The method of claim 3, wherein the dosage of the SBP that is fused to the immunostimulatory protein ranges from 25 microgram per kilogram body weight per day to 900 microgram per kilogram body weight per day.

5. A method of improving feed intake, growth rate, or feed conversion ratio in an animal in need thereof comprising to said subject by oral administration an effective amount of a composition comprising a complex consisting of a starch binding protein (SBP) that is fused to an immunostimulatory protein and a SBP-binding matrix, wherein the SBP consists of the amino acid sequence of SEQ ID NO: 3 and the immunomodulatory protein consists of the amino acid sequence of SEQ ID NO: 4.

6. The method of claim 5, wherein the dosage of the SBP that is fused to the immunostimulatory protein ranges from 25 microgram per kilogram body weight per day to 900 microgram per kilogram body weight per day.

7. The method of claim 1, wherein the *Eimeria* species is *Eimeria tenella*.

* * * * *